United States Patent [19]
Ellis et al.

[11] Patent Number: 5,632,268
[45] Date of Patent: May 27, 1997

[54] MULTIPLE PURPOSE FIXED OR PORTABLE OXYGEN DELIVERY SYSTEM

[76] Inventors: Donald L. Ellis, Rte. 3, Box 91; LeRoy J. Ellis, Rte. 3, Box 216, both of Cass Lake, Minn. 56633; Duane K. Rorie, 1040 Mayowood Rd. SW., Rochester, Minn. 55902

[21] Appl. No.: 595,744

[22] Filed: Feb. 2, 1996

[51] Int. Cl.$^6$ ............................................. A61M 16/00
[52] U.S. Cl. ........................... 128/204.18; 128/204.26; 128/205.21; 128/205.22; 128/200.29
[58] Field of Search ..................... 128/205.12, 204.18, 128/204.14, 204.15, 204.13, 200.25, 200.29, 204.26, 205.21, 205.22; 261/122.1, 126, DIG. 70

[56] References Cited

U.S. PATENT DOCUMENTS

| | | | |
|---|---|---|---|
| 754,317 | 3/1904 | Kaltenegger et al. | |
| 2,166,574 | 7/1939 | Adolphsen | 261/122.1 |
| 2,390,236 | 12/1945 | Boothby et al. | 128/205.12 |
| 2,936,542 | 5/1960 | Butler et al. | 43/57 |
| 2,947,525 | 8/1960 | Klein | 261/122.1 |
| 3,407,529 | 10/1968 | Kellner | 43/57 |
| 3,820,272 | 6/1974 | Rowe et al. | 43/57 |
| 3,957,007 | 5/1976 | Thomas | 114/116 |
| 4,034,030 | 7/1977 | Bracey | 261/64 |
| 4,181,126 | 1/1980 | Hendry | 128/201.21 |
| 4,300,496 | 11/1981 | Price | 128/202.13 |
| 4,501,270 | 2/1985 | Ulinskas | 128/202.13 |
| 4,649,912 | 3/1987 | Collins | 128/202.13 |
| 4,940,049 | 7/1990 | Kirchgeorg et al. | 128/204.18 |
| 4,944,292 | 7/1990 | Gaeke et al. | 128/204.18 |
| 5,123,409 | 6/1992 | Sheffield et al. | 128/204.18 |
| 5,256,282 | 10/1993 | Chang et al. | 261/122.1 |

*Primary Examiner*—Vincent Millin
*Assistant Examiner*—V. Srivastava
*Attorney, Agent, or Firm*—Haugen and Nikolai, P.A.

[57] ABSTRACT

An improved oxygen delivery system for use in a fishing vessel which is capable of distributing oxygen to individual fish and minnow live-well holding tanks for oxygenating the water within each such holding tank to sustain the fish and minnows therewithin, as well as distributing oxygen to a person in need of oxygen, such as in the case of a medical emergency.

17 Claims, 3 Drawing Sheets

MULTIPLE PURPOSE FIXED OR PORTABLE
OXYGEN DELIVERY SYSTEM

BACKGROUND OF THE INVENTION

I. Field of the Invention

The present invention relates generally to an oxygen delivery system for use in oxygenating the water within live-well holding tanks for fish and/or minnows. More particularly, the present invention relates to an improved oxygen delivery system for use in a fishing vessel which is capable of delivering oxygen to individual fish and minnow live-well holding tanks for sustaining the fish and minnows therewithin, as well as delivering oxygen to a person in need of oxygen, such as in the case of a medical emergency.

II. Discussion of the Prior Art

The sport of fishing is an endeavor which enjoys widespread acceptance by professional and casual fishermen alike, encompassing virtually every age group from young children to the elderly. With such sweeping support, the pool of fishermen necessarily includes a large number of people who have existing health problems or who are likely candidates to experience health problems. In particular, many fishermen may suffer from cardiovascular disease, a disorder which afflicts an enormous percent of the population and causes threat to literally millions of people worldwide. In the United States alone, cardiovascular disease results in approximately one million deaths each year, accounting for nearly one half of all deaths occurring within the United States per annum. More specifically, coronary artery disease is responsible for roughly one half of these cardiovascular disease deaths, afflicting an estimated 6.2 million people in the United States. Coronary artery disease impairs blood flow to the heart so that the heart is less effective as a pump and consequently becomes incapable of circulating a sufficient amount of blood throughout the body, which results in an increased risk of suffering from myocardial infarction and sudden death.

Sudden death due to coronary artery disease is a death that is not preceded by any condition that would appear fatal, and often occurs within two hours of the onset of symptoms. It is the most prominent medical emergency in the United States today and, alarmingly, approximately two-thirds of all such sudden deaths occur outside the hospital. Myocardial infarction, commonly referred to as a heart attack, is a condition caused by occlusion of one or more of the coronary arteries. The symptoms include prolonged heavy pressure or squeezing pain in the center of the chest, nausea, vomiting, sweating, and shortness of breath. Heart attacks may range in degree from mild to massive; however, not all heart attacks cause the heart to completely stop beating. In fact, in many instances the heart continues to beat but is simply incapable of adequately circulating the blood throughout the body. In either event, it is imperative that medical care be obtained without delay.

The major threat during a condition of improper blood circulation, or heart cessation, is the resultant decrease in the oxygen content of the blood. Insufficient oxygenation of the blood, known as hypoxemia, can cause severe changes in the metabolism of the body as well as metabolic and respiratory acidosis. This acidotic condition is particularly menacing in that it can frustrate actions taken to defibrillate the heart, as well as thwart or retard the beneficial effects of certain drugs that may be administered to aid the heart attack victim. Moreover, the lack of oxygen in the blood during a heart attack is capable of causing irreversible brain damage after only 5 to 10 minutes from the time the heart stops beating. To counteract these ill-effects of hypoxemia, the American Heart Association recommends that 100% oxygen be supplied to all persons suffering from a heart attack.

Contrary to popular belief, most heart attacks are not the product of heavy or excessive physical exertion. Rather, the majority of heart attacks strike while the victim is at rest or during periods of mild exertion, such as fishing. The sport of fishing typically involves a degree of traveling about a body of water in a vessel, such as a motor boat, in an effort to search for and catch fish. This traveling about necessarily increases the amount of time required to reach the safety of the shore for medical assistance in an emergency situation, such as during a heart attack. As noted above, time is of the essence during such an exigency to minimize or prevent a condition of insufficient blood oxygenation so as to avoid such complications as acidosis and irreversible brain damage.

A need therefore exists for providing an oxygen delivery system for a fishing vessel to aid any individuals therewithin who may be in need of oxygen, such as during a heart attack, stroke, or heat exhaustion. In addition, with the inherent spatial constraints of a fishing vessel, it would be advantageous to consolidate this need to provide oxygen for humans with the need to oxygenate the water within live-well holding tanks for sustaining fish and minnows while being transported within the fishing vessel. Such live-well holding tanks are common in the art and typically equipped with an oxygen supply tank and various regulators for metering oxygen into the water bath within the live-well holding tanks to keep the minnows and fish alive for long periods of time.

OBJECTS AND SUMMARY OF THE INVENTION

Accordingly, it is a primary object of the present invention to provide an oxygen distribution system for a fishing vessel capable of providing oxygen to any person who may be in need thereof.

It is another object of the present invention to provide an oxygen distribution system having the combined capability of oxygenating the water within any fish and/or minnow live-well holding tanks within the fishing vessel, as well as distributing oxygen to an individual during a medical emergency.

It is still another object of the present invention to provide an oxygen distribution system that is easy to install and maintain, low in cost, reliable, and safe.

It is a further object of the present invention to provide an oxygen distribution system of durable and compact construction suitable for convenient positioning within a fishing vessel.

It is yet another object of the present invention to provide an oxygen distribution system for fish, minnows, and humans having selective metering capability for conserving oxygen and prolonged operational life.

In accordance with a broad aspect of the present invention, an apparatus is provided comprising oxygen supply means for providing a predetermined supply of pressurized oxygen, and regulation means in fluid communication with the oxygen supply means for selectively dispensing the pressurized oxygen from the oxygen supply means. The regulation means further includes first metering means for selectively adjusting the flow of the pressurized oxygen to oxygen diffusion means, and second metering means for selectively adjusting the flow of the pressurized oxygen to oxygen mask means.

In another broad aspect of the present invention, disclosed is an oxygen distribution system for use with a fishing vessel having at least one holding tank having a water bath disposed therein, comprising oxygen supply means for supplying pressurized oxygen, regulation means associated with the oxygen supply means for controlling the egress of the pressurized oxygen from the oxygen supply means, diffusion means associated with the regulation means for placement within the water bath within the at least one holding tank, and oxygen mask means associated with the regulation means for supplying oxygen to a human being.

In yet another broad aspect of the present invention, a method of distributing oxygen is provided, comprising the steps of: (a) providing an oxygen distribution system including oxygen supply means for supplying pressurized oxygen, regulation means for controlling the egress of the pressurized oxygen from the oxygen supply means, oxygen diffusion means associated with the regulation means for placement within a water bath, and oxygen mask means for attachment to the regulation means; (b) selectively adjusting the regulation means to control the oxygenation of the water bath with the oxygen diffusion means; and (c) selectively attaching the oxygen mask means to the regulation means to supply oxygen to a victim.

DETAILED DESCRIPTION OF THE PREFERRED EMBODIMENTS

Figure 1:
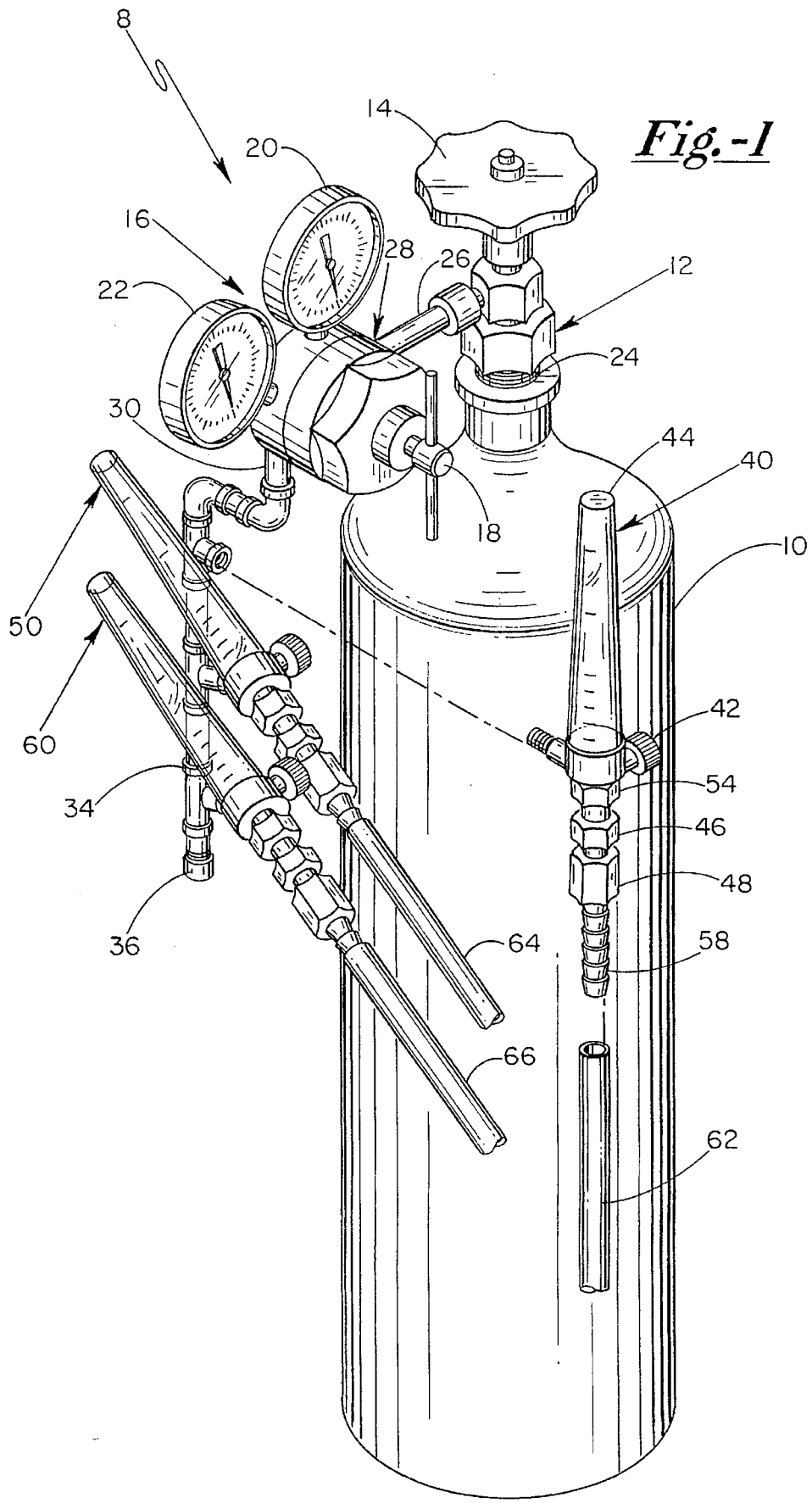
FIG. 1 is a general perspective view of the oxygen tank and regulator assembly of the present invention.
Figure 2:
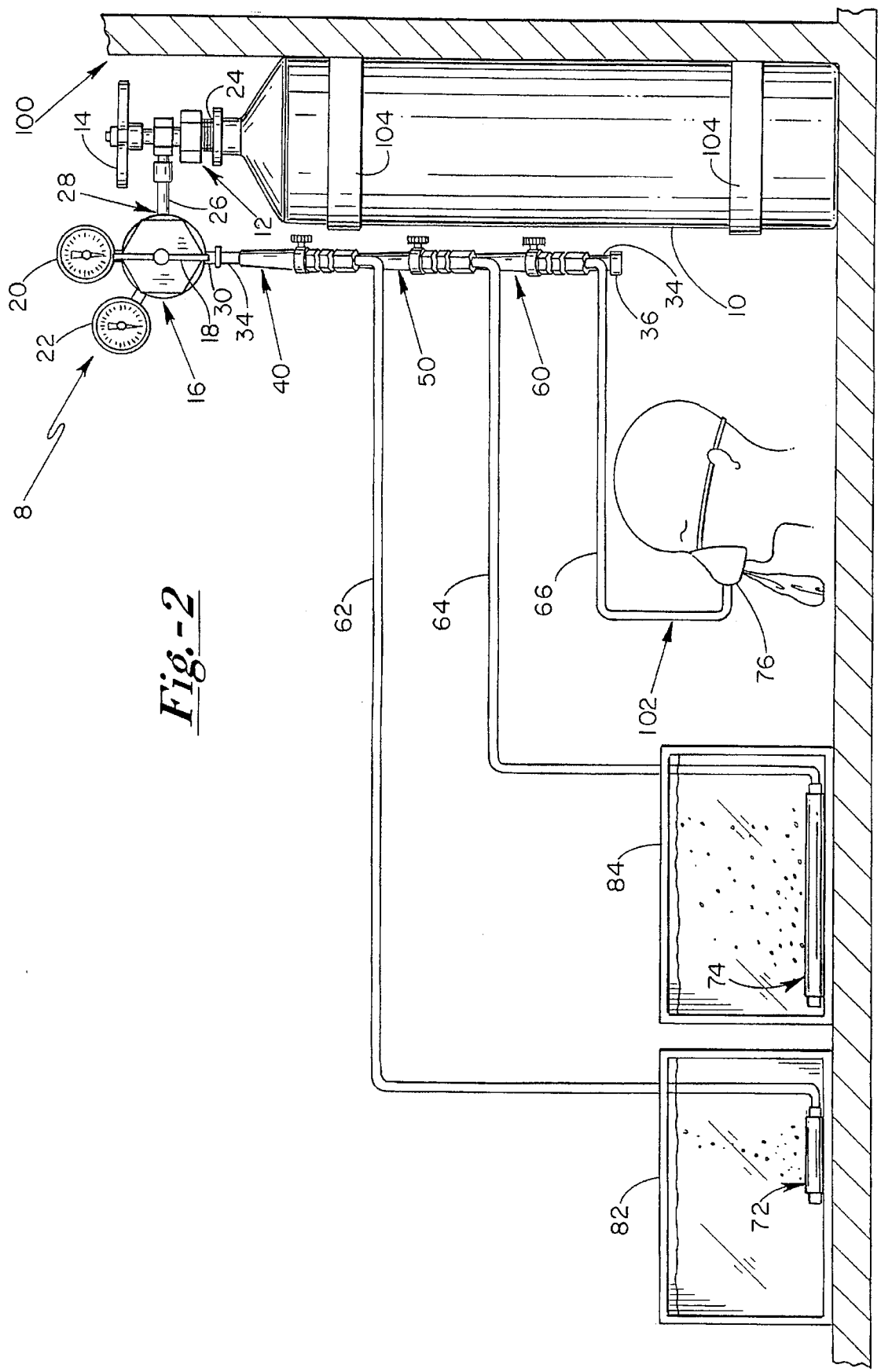
FIG. 2 is a schematic representation of the present invention.

Referring initially to FIGS. 1 and 2, shown is an oxygen distribution system of the present invention, referred to generally by reference numeral 8, for use in a fishing vessel, indicated generally as reference numeral 100. In an effort to achieve the aforementioned objects, oxygen distribution system 8 is provided with a high pressure oxygen tank 10 for supplying oxygen to a bait-well 82 and a catch-well 84 to provide an oxygenated water bath to sustain any bait and catch contained therein for prolonged periods of time. Moreover, in an important aspect of the present invention, oxygen distribution system 8 is capable of supplying oxygen to a person experiencing a medical emergency, such as a heart attack, stroke, or heat exhaustion.

Oxygen tank 10 is provided in fixed position within fishing vessel 100 through the use of strap members 104 or the like and is capable of being charged with a predetermined amount of pressurized oxygen through a threaded inlet/outlet port 24. In a preferred embodiment of the present invention, oxygen tank 10 comprises an oxygen cylinder of the type commonly found in the art, such as a 20 pound tank, charged with 20 cubic feet (660 liters) of oxygen, or a 40 pound tank, charged with 40 cubic feet (1320 liters) of oxygen. These examples are offered by way of illustration and not limitation, and it is to be understood that any number of oxygen cylinders having a wide range of shapes and sizes can be adapted for use in accordance with the present invention without departing from the scope thereof. A nozzle assembly 12 is threadably coupled within inlet/outlet port 24 for selectively permitting the pressurized oxygen within tank 10 to flow to a pressure regulator assembly 16. More specifically, the counter-clockwise rotation of a handle member 14 of nozzle assembly 12 opens up a flow path that leads from the inside of tank 10 to pressure regulator 16 via a first manifold 26.

Pressure regulator assembly 16 is provided with an inlet port 28 for threaded connection to first manifold 26, an outlet port 30 for threaded connection to a second manifold 34, and a handle member 18 for selectively adjusting an internally disposed valve (not shown) for controlling the amount of pressure being supplied to second manifold 34. Pressure regulator assembly 16 is further provided with a first pressure gauge 20 for indicating the oxygen pressure within tank 10 (and connecting manifold 26), and a second pressure gauge 22 for indicating the oxygen pressure being supplied to second manifold 34. In the preferred embodiment shown, second manifold 34 has a closed terminal end 36 opposite from outlet port 30 and is comprised of a plurality of interconnected segments of galvanized pipe. However, it is to be understood that second manifold 34 may be constructed of any number of materials capable of withstanding high pressures, including by not limited to stainless steel. Such a construction of galvanized or stainless steel piping is also advantageous due the characteristic resistance to corrosion and oxidation of such materials.

Figure 3:
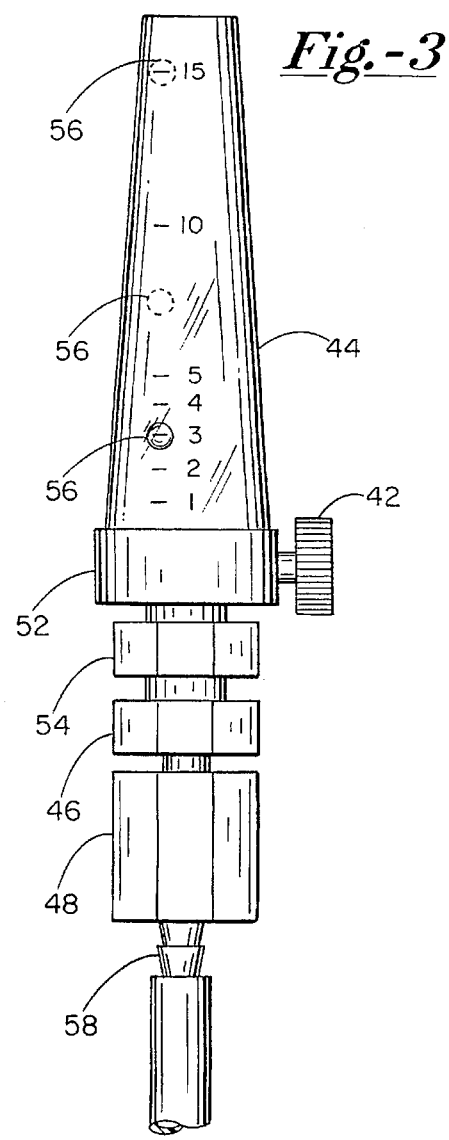
FIG. 3 is a partial sectional view of an oxygen diffuser of the present invention disposed in a water bath of a holding tank.

With reference to FIGS. 1–3, a first flow meter assembly 40, a second flow meter assembly 50, and a third flow meter assembly 60 are further provided, each threadably coupled to manifold 34 and identical in construction. As detailed specifically in FIG. 3, each flow meter assembly 40, 50, 60 includes a flow meter 52 having an inlet portion (not shown) for attachment to second manifold 34, an outlet portion 54, and an adjustment knob 42 for opening and closing an internally disposed valve (not shown) to control the flow of oxygen between second manifold 34 and the outlet portion 54 of flow meter 52. Flow meter 52 is further provided with a viewing cylinder 44 extending opposite outlet portion 54 for monitoring the rate of the oxygen flowing through the flow meter 52. To accomplish this, viewing cylinder 44 has gradations indicative of flow rates ranging between 0 to 15 liters/minute, while a flow rate indicator 56 is slidably disposed within the viewing cylinder 44. Flow meter 52 is calibrated such that flow rate indicator 56 floats to the appropriate gradation within viewing cylinder 44 depending upon the degree to which adjustment knob 42 is rotated to open or restrict the flow of oxygen through flow meter 52. In the preferred embodiment shown in FIG. 3, flow meter 52 is comprised of a model F26848 15 liter flow meter, such as is commercially available from any oxygen supply dealer.

Still referring to FIG. 3, first, second, and third flow meter assemblies 40, 50, 60 further include a one-way check valve 46 threadably coupled to the outlet portion 54 of flow meter 52. Check-valve 46 is attached to outlet portion 54 so as to permit an outward flow of oxygen from flow meter 52 toward an adapter 48 which is threadably coupled to check valve 52 while preventing any reverse flow back into the flow meter 52. The adapter 48 has a notched spout portion 58 for force-fit connection to a tubular member or hose section. In the preferred embodiment shown, check-valve 46 is a model CV-30R, produced by Western Enterprize. However, it is to be understood that any number of commercially available check-valves or flow meters may suffice without departing from the scope of the invention.

With collective reference to FIGS. 1–3, the water bath oxygenation feature of the present invention is as follows. A first tubular member 62 is provided with a proximal end attached to the notched spout portion 58 of first flow meter assembly 40 and a distal end attached to a first oxygen diffuser 72. In similar fashion, a second tubular member 64 is provided having a proximal end attached to the notched spout portion 58 of second flow meter assembly 50 and a distal end attached to a second oxygen diffuser 74. As can be seen, first oxygen diffuser 72 is submersed within the water bath of bait-well 82, while second oxygen diffuser 74 is submersed within the water bath of a catch-well 84. As will be explained in greater detail below, first and second oxygen diffusers 72, 74 are porous in construction such that a plurality of oxygen bubbles are dispersed within bait-well 82 and catch-well 84 when oxygen is supplied thereto. As such, oxygen may be selectively supplied to first oxygen diffuser 72 within bait-well 82 via flow meter assembly 40 to oxygenate the water bath therein to provide a sustaining environment for any bait, such as minnows, leaches, crayfish, or the like, prior to use in fishing. In similar fashion, the water bath within catch-well 84 may be selectively oxygenated via second flow meter assembly 50 and second oxygen diffuser 74 to sustain any catch, such as fish, prior to cleaning.

Figure 4:
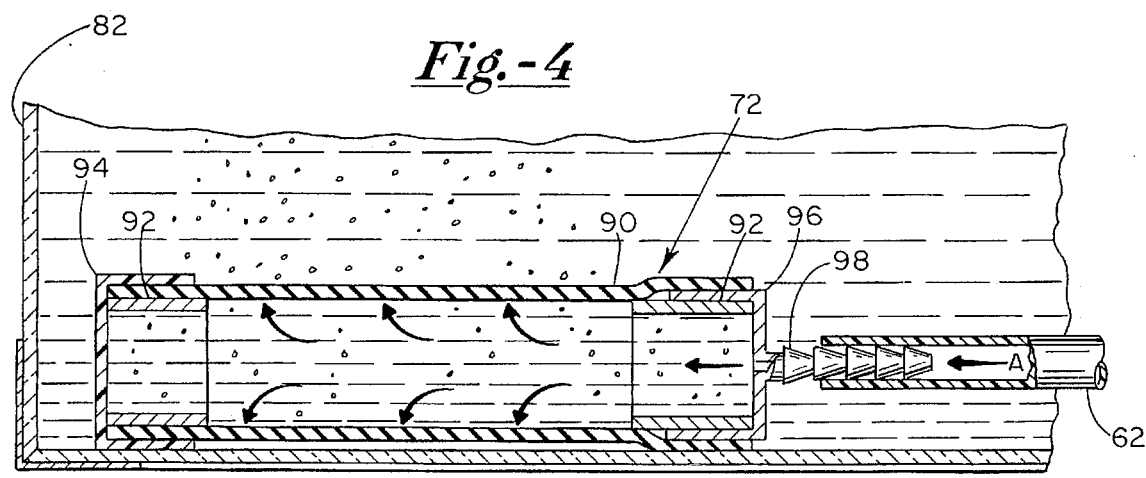
FIG. 4 is a side view of flow meter of the present invention.

Referring now to FIG. 4, shown is a partial sectional view detailing the construction of first oxygen diffuser 72. An elongated porous member 90 extends between an end cap 94 and an adapter 96 having a notched spout portion 98 for receiving first tubular member 62. Porous member 90 should preferably be long enough to extend substantially the entire length of bait-well 82 when disposed therein. While porous member 90 is shown as a generally elongated tubular member, it is to be understood that porous member 90 may comprise any number of shapes to accommodate the interior of bait-well 82, including zig-zag, circular, or horse shoe-type shapes. End cap 94 and oxygen adapter 96 may be constructed of any suitable material, including plastic and/or stainless steel. However, in the preferred embodiment shown, both end cap 94 and oxygen adapter 96 are plastic in construction. A pair of tubular weight members 92, such as segments of galvanized pipe, are disposed within end cap 94 and adapter 96 to ensure that first oxygen diffuser 72 is submersible within the water bath of first holding tank 82. In operation, oxygen flows from first flow meter assembly 40 through first tubular member 62 and notched spout portion 98 of adapter 96, as indicated by arrow A, and finally into the porous member 90. Due to the porous nature of porous member 90, the oxygen entering first oxygen diffuser 72 is emitted therefrom as a plurality of bubbles to thereby oxygenate the water bath of first holding tank 82.

Second oxygen diffuser 74 is constructed in essentially the same manner as first oxygen diffuser 72 and, therefore, an explanation as to the manufacture of second oxygen diffuser 74 is deemed duplicative and will not be repeated. The only exception, as shown in FIG. 2, is that second oxygen diffuser 74 may be required to be longer in length than first oxygen diffuser 72 due to the difference in length between first and second holding tanks 82, 84. Because the oxygen distribution system 8 of the present invention is for use within a fishing vessel, it follows that the first and second tubular members 62, 64 must be of sufficient length to reach first and second holding tanks 82, 84, respectively. In the preferred embodiment shown, first and second tubular members 62, 64 comprise plastic tubing with an inner diameter of 3/16 inch. However, it is to be understood that coated tubing material may be used on first and second tubular members 62, 64, such as metal mesh casing, so as to minimize unwanted and undesirable puncture thereof.

Referring once again to FIGS. 1-3, the emergency oxygen supply feature of the present invention is as follows. In the event that someone within fishing vessel 100, or in the immediate proximity of fishing vessel 100, suffers from a medical emergency requiring oxygen, such as a heart attack or stroke, an emergency oxygen assembly 102 is provided for immediate attachment to third flow meter assembly 60. Emergency oxygen assembly 102 comprises a third tubular member 66 having a proximal end for attachment to third flow meter assembly 60 and a distal end for attachment to an oxygen mask 76. Oxygen mask 76 may comprise any number of oxygen masks, including but not limited to a rebreather mask, for administering oxygen to a person who is capable of breathing on their own, and a pressure mask, for administering oxygen to a person who is incapable of breathing on their own. Such oxygen masks are commercially available and well known in the art. To ensure proper sterilization prior to use, emergency oxygen assembly 102 should preferably be contained in a hermetically sealed package within fishing vessel 100. Therefore, when needed, emergency oxygen assembly 102 may be quickly withdrawn and connected to third flow meter assembly 60 to supply oxygen to the person in need. To facilitate the administration of oxygen to a patient, third tubular member 66 is provided with sufficient length to extend to any point in and around fishing vessel 100 where a patient may rest, lie, or sit.

In an important aspect of the present invention, each flow meter 52 of the first, second, and third flow meter assemblies 40, 50, 60 may be selectively adjusted via adjustment knob 42 to dictate the flow of oxygen provided to first and second oxygen diffusers 72, 74 and oxygen mask 76. Through this arrangement, oxygen may be supplied in any combination to first and second oxygen diffusers 72, 74 and oxygen mask 76. For example, in the event that no fish have been caught and no medical emergency exists, only flow meter 52 of first flow meter assembly 40 would be opened to oxygenate the water bath within bait-well 82. In similar fashion, the present invention is capable of having each flow meter 52 of first, second, and third flow meter assemblies 40, 50, 60 opened at the same time to simultaneously deliver oxygen to bait-well 82, catch-well 84, and oxygen mask 76. However, in the case of a life-threatening emergency, it would be advantageous to stop or minimize the delivery of oxygen to bait-well 82 and catch-well 84 so as to conserve the oxygen remaining within oxygen tank 10 for administration to the patient during transportation to a hospital for medical assistance.

In this regard, it is important to note that oxygen distribution system 8 of the present invention is fully portable and therefore capable of providing oxygen to a patient between the point of reaching the shore and the point of reaching a hospital. This can be accomplished by simply removing strap members 104 from their fixed position about oxygen tank 10 and carrying oxygen tank 10 along with the patient during transportation to the hospital. To aid in this portability, it is advantageously provided that first and second oxygen diffusers 72, 74 may be detached from oxygen distribution system 8 so as to minimize the number of components that must accompany the patient on the trip to the hospital. To do so, a user need only close each flow meter 52 of first and second flow meter assemblies 40, 50 and then simply disconnect first and second tubular members 62, 64 therefrom for storage until later use.

Bait-well 82 and catch-well 84 may be constructed to form any number of shapes and sizes, and may be either formed as an integral part of fishing vessel 100 or positioned therein as an after-market accessory. Bait-well 82 may contain any number of baits used in fishing. However, in a typical application, bait-well 82 may contain a water bath of approximately 8 to 10 gallons and approximately 25 dozen minnows ranging from 1 to 3 inches in length. To adequately oxygenate this water bath to sustain the minnows, a flow rate of approximately ⅛ liter of oxygen per minute will be required. Referring to FIGS. 1–3, this flow rate may be attained by rotating adjustment knob 42 of first flow meter assembly 40 in a clock-wise manner until flow rate indicator 56 comes to a floating rest at the ⅛ liter mark of viewing cylinder 44. In a similar fashion, catch-well 84 may contain any number of fish or other aquatic catch. Therefore, the amount of oxygen being supplied to catch-well 84 should vary depending upon the fortune of the fishing outing, i.e. the number and size of the fish caught. For example, a flow rate of ½ liter of oxygen per minute would be required to properly support 4 to 5 fish ranging from ¾ pounds to 3 pounds, whereas an increased flow rate of approximately 2 liters of oxygen per minute would be required to sustain 10 or more large fish ranging between 2 and 10 pounds in weight.

As mentioned above, each flow meter 52 is adjustable between the flow rates of 0 and 15 liters per minute. While first and second flow meter assemblies 40, 50 are typically set at relatively low flow rates, third flow meter assembly 60 may be required to be set at substantially higher flow rates to adequately supply oxygen to a patient. For instance, with a rebreather oxygen mask 76, a flow rate of 6 liters of oxygen per minute will provide approximately 60% oxygen concentration in the air that is being inhaled by the patient, which is approximately three times greater than the oxygen content of the outside air. Under this configuration, the oxygen concentration being inhaled by the patient is increased in 10% intervals for every one liter per minute increase in flow rate. Therefore, a flow rate of 10 liters of oxygen per minute would result in an oxygen concentration of 100%.

This invention has been described herein in considerable detail to provide those skilled in the art with the information needed to apply the novel principles and to construct and use embodiments of the example as required. However, it is to be understood that the invention can be carried out by specifically different devices and that various modifications can be accomplished without departing from the scope and spirit of the above-describe invention.

For example, it is contemplated that oxygen tank 10 may be equipped with a protective cover for placement over nozzle assembly 12 so as to minimize any possibility of inadvertent damage. Along these lines, it is contemplated and urged that oxygen tank 10 be disposed in an upright position within fishing vessel 100, as shown in FIG. 2, such that oxygen tank 10 does not act as a projectile under the force of the escaping pressurized oxygen if nozzle 12 is severed from oxygen tank 10. Moreover, it is contemplated that a single oxygen diffuser may be required in the case of a single holding tank that is compartmentalized to have a minnow portion and a fish portion. It is similarly anticipated that second manifold 34 may be configured in any particular physical position relative to the oxygen tank, depending on the space constraints of the particular fishing vessel.

Therefore, in light of the foregoing, the present invention provides the capability of supplying oxygen to a person during a medical exigency, such as a heart attack, stroke, or heat exhaustion. Due to the pressurized supply of oxygen within oxygen tank 10, life-saving oxygen may be provided to the patient during transportation to shore and/or the arrival of medical personnel. Administration of oxygen during this time period reduces the risk to the patient of experiencing brain damage or respiratory acidosis during a condition of improper blood circulation. Moreover, the present invention provides such life-saving capability in an efficient and low cost manner by combining it with a device for oxygenating the water baths of any bait-well or catch-well disposed within the fishing vessel.

What is claimed is:

1. An apparatus, comprising:
    oxygen supply means for providing a predetermined supply of pressurized oxygen;
    regulation means in fluid communication with said oxygen supply means for selectively dispensing said pressurized oxygen from said oxygen supply means, said regulation means including first metering means and second metering means;
    oxygen diffusion means connected to said first metering means for diffusing oxygen within a water bath, said first metering means for selectively adjusting the flow of said pressurized oxygen to said oxygen diffusion means; and
    oxygen mask means connected to said second metering means for delivering oxygen to a patient in need of oxygen, said second metering means for selectively adjusting the flow of said pressurized oxygen to said oxygen mask means.

2. The apparatus set forth in claim 1 and further, said oxygen diffusion means comprising at least one submersible porous member for placement within said water bath.

3. The apparatus set forth in claim 2 and further, said oxygen mask means comprising one of a breather mask and a pressure mask.

4. The apparatus set forth in claim 3 and further, said second metering means comprising at least one flow meter for selectively supplying said pressurized oxygen to said oxygen mask means.

5. The apparatus set forth in claim 3 and further, said first metering means comprising at least one flow meter for selectively supplying said pressurized oxygen to said oxygen diffusion means.

6. The apparatus set forth in claim 5 and further, including first check valve means associated with said first metering means for permitting an outward flow of said pressurized oxygen to said oxygen diffusion means and second check valve means associated with said second metering means for permitting an outward flow of said pressurized oxygen to said oxygen mask means.

7. The apparatus as set forth in claim 2 and further, said at least one submersible porous member having a generally hollow construction with a plurality of oxygenation pores extending about the periphery of said porous member, said porous member having at least one internally disposed weight member for maintaining said submersible porous member under a surface of said water bath.

8. An oxygen distribution system for use with a fishing vessel having at least one holding tank having a water bath disposed therein, comprising:
    oxygen supply means for supplying pressurized oxygen;
    regulation means associated with said oxygen supply means for controlling the egress of said pressurized oxygen from said oxygen supply means;
    oxygen diffusion means associated with said regulation means and disposed within said water bath within said at least one holding tank, said oxygen diffusion means for oxygenating said water bath within said at least one holding tank; and oxygen mask means for connection to said regulation means for supplying oxygen to a human being in need of oxygen.

9. The oxygen distribution system set forth in claim 8 and further, said oxygen diffusion means comprising at least one submersible oxygen diffuser including an elongated porous member for introducing said pressurized oxygen from said oxygen supply means into said water bath within said at least one holding tank.

10. The oxygen distribution system set forth in claim 9 and further, said regulation means including first flow meter means for selectively adjusting the flow rate of said pressurized oxygen to said oxygen diffusion means and second flow meter means for selectively adjusting the flow rate of said pressurized oxygen to said oxygen mask means.

11. The oxygen distribution system set forth in claim 10 and further, said oxygen mask means comprising a mask member for placement over the face of said victim, and a hose member having a first end for attachment to said second flow meter means and a second end for attachment to said mask member.

12. The oxygen distribution system set forth in claim 11 and further, said mask member comprising one of a breather mask and a pressure mask.

13. The oxygen distribution system as set forth in claim 9 and further, said elongated porous member having a generally hollow construction with a plurality of oxygenation pores extending about the periphery thereof, said at least one submersible oxygen diffuser including at least one substantially solid weight member disposed within said porous member for maintaining said porous member under a surface of said water bath.

14. A method of distributing oxygen, comprising the steps of:

(a) providing an oxygen distribution system including oxygen supply means for supplying pressurized oxygen, regulation means for controlling the egress of said pressurized oxygen from said oxygen supply means, oxygen diffusion means associated with said regulation means for placement within a water bath, and oxygen mask means for attachment to said regulation means;

(b) adjusting said regulation means to control the oxygenation of said water bath with said oxygen diffusion means; and (c) attaching said oxygen mask means to said regulation means to supply oxygen to a victim during a medical emergency.

15. The method set forth in claim 14 and further, step (a) comprising the further sub-steps of: (i) providing first flow meter means extending between said regulation means and said oxygen diffusion means; and (ii) providing second flow meter means extending between said regulation means and said oxygen mask means.

16. The method set forth in claim 15 and further, step (b) comprising the further sub-step of selectively adjusting said first flow meter means to control the oxygenation of said water bath with said oxygen diffusion means.

17. The method set forth in claim 16 and further, step (c) comprising the further sub-steps of: (i) placing said oxygen mask means over the mouth and nose of said victim; and (ii) selectively adjusting said second flow meter means to control the supply oxygen to said victim.

* * * * *